United States Patent [19]

Sandler

[11] Patent Number: 4,546,205
[45] Date of Patent: Oct. 8, 1985

[54] STABILIZATION OF ALDEHYDES

[75] Inventor: Stanley R. Sandler, Springfield, Pa.

[73] Assignee: Pennwalt Corporation, Philadelphia, Pa.

[21] Appl. No.: 389,150

[22] Filed: Jun. 16, 1982

[51] Int. Cl.$^4$ .................. C07C 45/86; C09K 15/16; C09K 15/22

[52] U.S. Cl. .................. 568/421; 252/401; 252/403; 568/19; 568/422

[58] Field of Search .......... 568/19, 421, 422; 252/401, 403

[56] References Cited

U.S. PATENT DOCUMENTS 2,912,468  11/1969  Copenhaver .................. 568/58

FOREIGN PATENT DOCUMENTS 153227   1/1951  Australia .
218809   7/1957  Australia .
40-24605 10/1965  Japan .
47-32963  8/1972  Japan .

OTHER PUBLICATIONS

Baxter, Kirk–Othmer, "Encyl. of Chem. Tech.", 7, (3rd Ed.) p. 207 (1979).
C.A. 82, 155340c (1975).
C.A. 77, 139425a (1972).
C.A. 70, 37190H (1969).
C.A. 53, 280 (1959).

*Primary Examiner*—Natalie Trousof
*Assistant Examiner*—Vera C. Clarke

[57] ABSTRACT

An amino/phenolic composition effective for enhancing the storage stability of aldehydes, particularly sulfur-containing aliphatic aldehydes of low molecular weight, i.e., those containing from 3 to 10 carbon atoms.

7 Claims, No Drawings

STABILIZATION OF ALDEHYDES

BACKGROUND

Aldehydes are known to undergo degradation upon storage through polymerization and acetal formation. Thus, often aldehydes must be purified by distillation before use; the presence of degradation products affects not only the concentration of the active aldehyde but also the impurities (sometimes color-forming) often interfere in chemical reactions involving the aldehyde. It is not uncommon in commercial applications where an aldehyde is to be used in the manufacture of fine chemicals to have a specification requiring the product to be 96% pure with less than 1% non-volatiles. It is an object of this invention to stabilize aldehydes against degradation on storage.

PRIOR ART

Various stabilizers to prevent degradation on storage have been reported for aldehydes, such as either hydroquinone or water for crotonaldehyde [W. F. Baxter, Jr., in Kirk-Othmer's *Encycl. of Chem. Technol.*, 7, (3rd Ed) 207 (1979)], N,N-dialkylanilines for 3-(methylthio)propionaldehyde [Japan Kokai No. 74 116,017 Sept. 27, 1974; *Chem. Abstr.*, 82, 155340c (1975)] and pyridine as well as 2,4,6-collidine, lutidine or quinoline for the same sulfur containing aldehyde. [Japan 72 32,963 Aug. 22, 1972; *Chem. Abstr.*, 77, 139425a (1972)]. Butyraldehyde has been reported to be stabilized by ethylenediamine tetraacetic acid (EDTA) and the stabilizer is reported to prevent color formation [Japan 68 18,125 Aug. 1, 1968; *Chem. Abstr.*, 70, 37190h (1969)]. The oxidation of butyraldehyde, benzaldehyde and tolualdehyde are also reported to be inhibited by the presence of either hydroquinone, phenol, sulfuric acid or large quantities of water or ethanol [L. G. Marukovakaya et. al., Trudy Inst. Khim. Nauk, Akad Nauk Kazakh S.S.S.R., 2 188 (1958); *Chem. Abstr.*, 53, page 280 (1959)].

Low molecular weight aliphatic aldehydes containing sulfur, i.e. those containing from 3 to 10 carbon atoms, are particularly susceptible to degradation that produces oligomers and polymers. In the case of 3-(ethylthio)butanal (3-ETB), the dithioacetal by-products have been reported to be readily polymerized in the presence of traces of acids acting as catalysts (see U.S. Pat. No. 2,912,468, dated Oct. 10, 1959). There is no published art known to applicant teaching stabilization of 3-ETB against degradation on storage. The usual aldehyde-stabilizers such as pyridine, hydroquinone and EDTA are not effective in preventing the formation of oligomers and polymers when 3ETB is aged at room temperature or at 50° C.

THE INVENTION

The present invention provides an amino/phenolic composition effective for enhancing the storage stability of aldehydes, particularly sulfur-containing aliphatic aldehydes of low molecular weight, i.e. those containing from 3 to 10 carbon atoms. Since the stabilizing composition is used in only trace amounts and is completely soluble in the aldehyde, it does not interfere in most processes or reactions in which such aldehydes are used.

Suitable phenols for this invention are phenols, napthols, and anthranols optionally substituted by one or more hydrocarbyl, halogen, alkoxy, or hydroxyl groups. Examples are phenol, hydroquinone, dihydroanthraquinone, 4-methoxynaphthol, 4-methoxyphenol (MEHQ), 4-amylphenol, 2,4-diamylphenol, 2,4-dibutylphenol, 2,6-dibutylphenol and 2,6-di-t-butyl-4-methylphenol (BHT) and mixtures thereof.

Suitable amines are pyridine, picolines, lutidines, collidines and quinolines optionally substituted by one or more hydrocarbyl, halogens, alkoxy, or hydroxyl groups and mixtures thereof.

The molar proportion of the phenolic component to the amine is not important and may vary from 1:50 to 50:1 of amine:phenol. The phenolic component and the amine can be mixed together prior to the addition to the aldehyde or they also can be separately added to the aldehyde to be stabilized. As little as 100 ppm of stabilizing composition in an aldehyde will usually show some ability to prevent formation of degration products although use of about 1000 ppm is preferred. Higher concentration of stabilizer, e.g. up to 5000 ppm can often be tolerated but are generally avoided in the interest of economy.

The preferred stabilization composition is 4-methoxyphenol and pyridine in equimolar proportions or wherein the mole ratio of 4-methoxyphenol (MEHQ) to pyridine is within the limits of 20 to 1 to 40 to 1. It is preferred to employ such compositions in aldehydes within a concentration of 500 to 2000 ppm of stabilizer.

The stabilizing composition of the present invention is particularly useful in providing stabilization against degradation upon storage for low molecular weight sulfur-containing aldehydes having the formula

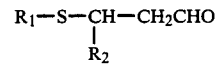

wherein $R_1$ is lower alkyl and $R_2$ is hydrogen or lower alkyl. Representative specific aldehydes within the defined class include 3-(methylthio)butanal, 3-(propylthio)butanal, 3-(ethylthio)butanal, 3-(methylthio)propional, 3-(butylthio)butanal, 3-(ethylthio)propional, 3-(propylthio)propional, and 3-(butylthio)propional. In addition, the stabilizing composition is effective in stabilizing non-sulfur containing aldehydes such as acrolein, crotonaldehyde, acetaldehyde, propionaldehyde, butyraldehyde, benzaldehyde and tolualdehyde.

In the case where the aldehyde is relatively insoluble in water, such as 3-(ethylthio)butanal, it is frequently helpful if the aldehyde is first washed with water and thereafter stabilized with the claimed composition.

The following example illustrates this invention and is not to be taken as a limitation thereof. An accelerated storage stability test is employed upon the sample stabilized pursuant to the present invention as well as the control and comparative control samples wherein each is sealed in a glass vial containing a Teflon coated neoprene septum seal in an aluminum cap. The cap is crimped closed and the vial placed in a 50° C. oven. Periodically a small sample is removed with a hypodermic syringe and the 3-ETB content is measured by gas chromatography. The non-volatiles are determined by heating a 1-3 g sample at 100° C. for 3 hours at 4 mm Hg. Gas chromatography also detects high-boilers in the 3-ETB and these may be present as well in the non-volatiles as determined in a separate determination. The non-volatiles determination gives a measure of the polymeric and non-gas chromatographical material that is present in the sample.

EXAMPLE

Two portions of a water-washed sample of 3-ETB were tested for storage stability and analyzed as described above; embodiment (a) contained 1000 ppm of MEHQ and 25 ppm of pyridine (i.e. approximately equimolar proportion) while embodiment (b) containing no added stabilizer (other than water) acted as a control; embodiment (a) was tested for 56 days and embodiment (b) for 57 days. The results are reported in Table I.

TABLE I

| Embodiment | % 3-ETB* | % Non-Volatiles |
|---|---|---|
| (a) | 97.0 | 0.42 |
| (b) | 87.1 | 1.73 |

*Uncorrected for non-volatiles (area % in gc)

It will be apparent from the above that the stabilized aldehyde lost substantially less active material on storage and formed substantially less non-volatiles (i.e. oligomers and polymers).

In further comparative samples, embodiments (c), (d) and (e) were tested for 56 days and analyzed as described above in which additives to water-washed 3-ETB were respectively 25 ppm of pyridine, 1000 ppm MEHQ and 1000 ppm BHT. The results are reported in Table II.

TABLE II

| Embodiment | % 3-ETB* | % Non-Volatiles |
|---|---|---|
| (c) | 97.2 | 4.1 |
| (d) | 86.9 | 9.8 |
| (e) | 87.0 | 4.0 |

*Uncorrected for non-volatiles (area % in gc)

From the above it will be observed that while embodiment (c) is comparable as far as preservation of active aldehyde is concerned, it is below even control embodiment (b) to which no stabilizer was added with respect to non-volatiles. Embodiment (d) and (e) are unsatisfactory on both formation of non-volatiles and preservation of active aldehyde.

Many obvious modifications of the above will be apparent to those skilled in the art without a departure from the inventive concept.

What is claimed is:

1. An aldehyde having the formula

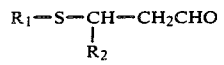

wherein $R_1$ is lower alkyl and $R_2$ is hydrogen or lower alkyl, said aldehyde containing from 100 to 2000 ppm of a stabilizer for aldehydes consisting essentially of a combination of: (a) a phenolic compound selected from the class consisting of phenols, napthols, or anthranols and mixtures thereof; and (b) an amine selected from the class consisting of pyridine, picoline, lutidine, collidine and quinoline, and mixtures thereof; wherein the phenolic and amine compounds can optionally be substituted with hydrocarbyl, halogen, alkoxy, or hydroxyl groups.

2. The aldehyde of claim 1 wherein the mole ratio of amine to phenolic compound varies from 1:50 to 50:1.

3. A stabilizer for an aldehyde consisting essentially of a substantially equimolar mixture of 4-methoxyphenol and pyridine.

4. The process of stabilizing an aldehyde having the formula

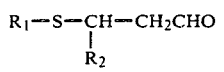

wherein $R_1$ is lower alkyl and $R_2$ is hydrogen or lower alkyl which comprises washing said aldehyde with water and thereafter adding a stabilizing amount of a stabilizer for an aldehyde consisting essentially of a substantially equimolar mixture of 4-methoxyphenol and pyridine.

5. The composition of claim 1 wherein the aldehyde is 3-(ethylthio)butanal.

6. The composition of claim 1 wherein the aldehyde is 3-(methylthio)propional.

7. A composition of matter consisting essentially of (i) a sulfur-containing low molecular weight aldehyde and (ii) a relatively minor amount of the stabilizer of claim 3 but sufficient to provide stability against degradation on storage to said composition.

* * * * *